(12) United States Patent
Moretti et al.

(10) Patent No.: US 7,973,200 B2
(45) Date of Patent: *Jul. 5, 2011

(54) PATCHOULOL ODORANT

(75) Inventors: Robert Moretti, Grand-Lancy (CH); Olivier Etter, Chene-Bourg (CH)

(73) Assignee: Firmenich SA, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/738,737

(22) PCT Filed: Oct. 29, 2008

(86) PCT No.: PCT/IB2008/054491
§ 371 (c)(1),
(2), (4) Date: Apr. 19, 2010

(87) PCT Pub. No.: WO2009/066193
PCT Pub. Date: May 28, 2009

(65) Prior Publication Data
US 2010/0209372 A1    Aug. 19, 2010

(30) Foreign Application Priority Data

Nov. 19, 2007   (WO) ................. PCT/IB2007/054690

(51) Int. Cl.
*C07C 39/14* (2006.01)
*C07C 35/00* (2006.01)
*C07C 69/76* (2006.01)
*A61K 8/18* (2006.01)
*C11D 3/40* (2006.01)

(52) U.S. Cl. .......... 568/736; 568/819; 560/100; 512/19; 510/104

(58) Field of Classification Search .................. 568/736; 560/100; 512/19; 510/104
See application file for complete search history.

(56) References Cited

U.S. PATENT DOCUMENTS

| | | | |
|---|---|---|---|
| 4,339,467 A | 7/1982 | Yoshida | 426/538 |
| 4,671,798 A | 6/1987 | Tarchini | 8/522 |
| 6,008,186 A * | 12/1999 | Schulte-Elte et al. | 512/17 |
| 7,378,383 B2 * | 5/2008 | Moretti et al. | 512/15 |
| 7,683,023 B2 * | 3/2010 | Gaudin | 512/1 |

FOREIGN PATENT DOCUMENTS

| | | |
|---|---|---|
| EP | 0 047 154 A2 | 3/1982 |
| EP | 0 167 709 A2 | 1/1986 |
| EP | 1 605 035 A1 | 12/2005 |

OTHER PUBLICATIONS

International Search Report and the Written Opinion of the International Searching Authority, application No. PCT/IB2008/054491, Feb. 26, 2009.

\* cited by examiner

*Primary Examiner* — Sikarl Witherspoon
(74) *Attorney, Agent, or Firm* — Winston & Strawn LLP

(57) ABSTRACT

The invention relates to the use as perfuming ingredients of 8a-alkyl-perhydro-naphthalenol derivatives, to impart odor notes of the woody-earthy type.

13 Claims, No Drawings

PATCHOULOL ODORANT

This application is a 371 filing of International Patent Application PCT/IB2008/054491, filed Oct. 29, 2008.

TECHNICAL FIELD

The present invention relates to the field of perfumery. More particularly, it concerns some perhydro naphthalenol derivatives of formula (I) which are useful as woody-earthy odorants. The present invention concerns the use of said compounds in the perfumery industry as well as the compositions or articles containing said compounds.

PRIOR ART

To the best of our knowledge, the invention's compounds are new, and have no close structural analogues which are known as perfuming ingredients.

DESCRIPTION OF THE INVENTION

We have now surprisingly discovered that a compound of formula

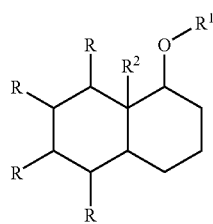

(I)

wherein $R^1$ represents a hydrogen atom or a formyl or acetyl group;
$R^2$ represents a methyl or ethyl group; and
each R represents, independently from each other, a hydrogen atom or a methyl group, and at least two of said R are methyl groups;
can be used as perfuming ingredient, for instance to impart odor notes of the woody-earthy type.

According to an embodiment of the invention, said compound (I) is one wherein $R^1$ is a hydrogen atom.

According to an embodiment of the invention, said compound (I) is one wherein $R^2$ is a methyl group.

According to an embodiment of the invention, said compound (I) is of formula

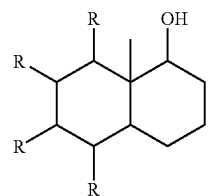

(II)

wherein two R represent hydrogen atoms and the two other R represent methyl groups.

As typical examples of the invention's compounds, one may cite perhydro-6,8,8a-trimethyl-1-naphthalenol. Said compound possesses a woody-earthy odor, combined with an interesting herbaceous-eucalyptus bottom note. The woody note lacks any amber connotation, which is often present in woody odorant being naphthalene derivatives. Furthermore, the overall odor, and in particular the earthy note, is very close to the odor of the forest floor, and in fact reminds very strongly of the odor of pure patchoulol. From a perfumistic or odor point of view, perhydro-6,8,8a-trimethyl-1-naphthalenol represents the closest synthetic analogue of pure patchoulol.

Furthermore the present compound distinguishes itself from the other perfuming ingredients having patchouli type note by lacking the phenolic, spicy notes so typical of patchouli oil.

It is also interesting to point out that perhydro-6,8,8a-trimethyl-1-naphthalenol demonstrated in various detergent tests to be amongst the most substantive compounds of its odor family.

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing compound (I) and which can be advantageously employed in perfumery industry as active ingredients.

Said compositions, which in fact can be advantageously employed as perfuming ingredient, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:

i) as perfuming ingredient, at least one compound of formula (I), as defined above, or an invention's perfuming composition; and
ii) a consumer product base;

is also an object of the present invention.

For the sake of clarity, it has to be mentioned that, by "consumer product base", we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 30% by weight, or even more, of the compounds of the invention based on the weight of the composition into which they are incorporated. Concentrations lower than these, such as in the order of 0.01% to 10% by weight, can be used when these compounds are incorporated into perfumed articles, percentage being relative to the weight of the article.

The invention's compounds were prepared by reacting an adequate cyclohexenone with an adequate diene (under Diels-Alder conditions) and then fully reducing the naphthalenone obtained. The examples herein below provided specific examples of this synthetic approach.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacements δ are indicated in ppm with respect to TMS as standard, the coupling constants J are expressed in Hz.

Example 1

Synthesis of perhydro-6,8,8a-trimethyl-1-naphthalenol

I) General Procedure for the Diels-Alder Coupling

In a 500 ml reactor were introduced AlEtCl$_2$, or AlCl$_3$, 0.1 g of BHT and toluene, or CH$_2$Cl$_2$. Then, under vigorous stirring, was added the appropriate cyclohexenone dropwise, so as to maintain the temperature below 30° C. Afterwards was added the diene dropwise and, when the reaction ended, the reaction mixture was hydrolyzed with 5% aqueous HCl, extracted twice with Et$_2$O. The organic layer was then washed with a saturated NaHCO$_3$ aqueous solution, water, brine and then dried over Na$_2$SO$_4$. Evaporation of the solvents, chromatography (SiO$_2$, elution heptane/AcOEt 98:2) and distillation provided the unsaturated naphthalenone.

II) General Procedure for the Hydrogenation of the Unsaturated Naphthalenone into the Perhydro Naphthalenone In a 100 ml flask were introduced the appropriate unsaturated naphthalenone, ethyl acetate and 10% w/w, relative to the unsaturated naphthalenone, of Pd/C 5%. The mixture was thus stirred under H$_2$, at a room temperature, until consumption of the theoretical amount of hydrogen. Afterwards, the reaction mixture was filtered over Nylon 6/6. Evaporation of the solvents and distillation provided the perhydro naphthalenone.

III) General Procedure for the Reduction of the Perhydro Naphthalenone into the Perhydro Naphthalenol In a 100 ml flask, maintained under Ar atmosphere, were introduced 2 molar equivalents, with respect of the ketone, of LiAlH$_4$ in Et$_2$O. Then the appropriate perhydro naphthalenone was added dropwise, so as to maintain the reflux. After completion of the reaction, the mixture was stirred for 30 minutes at reflux. Afterwards the reaction mixture was hydrolyzed with a stoechiometric amount of aqueous NaOH and the organic layer was dried over Na$_2$SO$_4$. Evaporation of the solvents and distillation provided the perhydro naphthalenol.

6,8,8a-trimethyl-3,4,4a,5,8,8a-hexahydro-1(2H)-naphthalenone

Prepared according to general procedure I), with the following quantities:

2-Methyl-2-cyclohexen-1-one (22 g; 0.2 mol)

Ethyl aluminium dichloride (1 molar solution in hexanes; 40 ml; 0.04 mol) Methylpentadiene (24.6 g; 0.3 mol), Dichloromethane (200 ml)

The title product was obtained in 50% yield (two isomers; GC ratio=27.2:72.8)

B.p.=85° C. (0.015 mbar)

$^1$H-NMR: 0.78 (d, J=7, 0.75H); 0.91 (s, 0.75H); 1.18 (d, J=7, 2.25H); 1.32 (s, 2.25H); 1.44-2.30 (m, 8H); 1.63 (broad s, 2.25H); 1.68 (broad s, 0.75H); 2.58-2.75 (m, 2H); 5.09 (broad s, 0.25H); 5.23 (broad s, 0.75H).

Perhydro-6,8,8a-trimethyl-1-naphthalenone

Prepared according to general procedure II), with the following quantities:

6,8,8a-trimethyl-3,4,4a,5,8,8a-hexahydro-1(2H)-naphthalenone (9.60 g, 0.05 mol) 5% Pd—C (1.0 g), EtOAc (100 ml)

The title product was obtained in 97% yield, as a mixture of isomers (GC ratio=66:22:6:6).

B.p.=75° C. (0.071 mbar)

$^1$H-NMR: 0.61-1.25 (m, 8H); 1.30-1.50 (m, 7H); 1.55-2.32 (m, 6H); 2.50-2.65 (m, 1H).

Perhydro-6,8,8a-trimethyl-1-naphthalenol

Prepared according to general procedure III), with the following quantities:

Perhydro-6,8,8a-trimethyl-1-naphthalenone (3 g, 0.016 mmol)

Lithium aluminium hydride (0.31 g, 0.008 mol), Diethylether (30 ml)

The title compound was obtained in 98% yield, as a mixture of isomers (GC ratio=64:31:5).

B.p.=86° C. (0.027 mbar)

$^1$H-NMR: 0.82-1.05 (m, 9H); 1.12-1.54 (m, 9H); 1.60-2.18 (m, 5H); 3.30-3.60 (m, 1H).

Example 2

Preparation of a Perfuming Composition

A perfume for a softener base, of the floral-violette type, was prepared by admixing the following ingredients:

| Ingredients | Parts by weight |
| --- | --- |
| Hexyl acetate | 20 |
| Benzyl acetate | 30 |
| Anisic aldehyde | 15 |
| C 11 Lenic eldehyde | 10 |
| C 12 Aldehyde | 10 |
| Hexylcinnamic aldehyde | 60 |
| MNA Aldehyde | 10 |
| 10% Aldolone ® [1] | 15 |
| Methyl anthranilate | 5 |
| Citronellol | 20 |
| 4-Cyclohexyl-2-methyl-2-butanol | 30 |
| Damascone Alpha | 5 |
| Decal | 10 |
| Dihydromyrcenol | 30 |
| Eugenol | 45 |
| Geraniol | 20 |
| Habanolide ® [2] | 75 |
| 1,3-Benzodioxole-5-carbaldehyde | 5 |
| Helvetolide ® [3] | 25 |
| Hivernal ® [4] | 15 |
| Iralia ® [5] Total | 30 |
| Lihal ® [6] | 120 |
| Linalol | 50 |
| Lorysia ® [7] | 50 |
| Hedione ® [8] | 70 |
| 10% * Neobutenone ® [9] Alpha | 10 |
| Rose oxide | 5 |
| Phenylhexanol | 30 |
| Hexyl salicylate | 75 |
| 2,2,7/8,9/10-Tetramethylspiro[5.5]undec-8-en-1-one | 10 |
| Undecavertol | 15 |
| Vanilline | 5 |
| Ionone alpha | 15 |
| | 940 |

* in dipropyleneglycol
[1] 7-propyl-2h,4h-1,5-benzodioxepin-3-one; origin: Firmenich SA, Switzerland
[2] pentadecenolide; origin: Firmenich SA, Switzerland
[3] (1S,1'R)-2-[1-(3',3'-dimethyl-1'-cyclohexyl)ethoxy]-2-methylpropyl propanoate; origin: Firmenich SA, Switzerland
[4] 3-(3,3/1,1-dimethyl-5-indanyl)propanal; origin: Firmenich SA, Switzerland
[5] Mixture of methyl ionones; origin: Firmenich SA, Switzerland
[6] 3-(4-tert-butylphenyl)-2-methylpropanal; origin: Givaudan-Roure SA, Vernier, Switzerland
[7] 4-(1,1-dimethylethyl)-1-cyclohexyl acetate; origin: Firmenich SA, Switzerland
[8] Methyl dihydrojasmonate; origin: Firmenich SA, Switzerland
[9] 1-(5,5-dimethyl-1-cyclohexen-1-yl)-4-penten-1-one; origin: Firmenich SA, Switzerland The addition of 60 parts by weight of perhydro-6,8,8a-trimethyl-1-naphthalenol brings a nice Patchouli effect to this fabric softener fragrance, even more striking on dry cloth.

Example 3

Preparation of a Perfuming Composition

An eau de cologne for man, of the woody-herbaceous type, was prepared by admixing the following ingredients:

| Ingredients | Parts by weight |
| --- | --- |
| Benzyl acetate | 30 |
| Linalyl acetate | 140 |
| Isobornyl acetate | 70 |
| Armoise essential oil | 50 |
| Cashmeran ® [1] | 10 |
| Cetalox ® [2] Laevo | 10 |
| Lemon essential oil | 60 |
| 4-Cyclohexyl-2-methyl-2-butanol | 100 |
| Coumarine | 130 |
| 10% * Ethylvanilline | 10 |
| Eugenol | 125 |
| Geranium essential oil | 20 |
| Habanolide ® [3] | 250 |
| Hedione ® [4] HC | 50 |
| Hydroxycitronellal | 20 |
| 10% * Indol | 10 |
| Iso E Super ® [5] | 500 |
| 10% * Isobutylquinoleine | 60 |
| Isojasmone | 20 |
| Lilyflore ® [6] | 40 |
| Linalol | 100 |
| Spearmint | 15 |
| Mousse Cristal | 75 |
| Muscenone [7] Delta | 55 |
| Dextro trans-1-(2,2,6-trimethyl-1-cyclohexyl)-3-hexanol | 10 |
| Pine essential oil | 50 |
| Rosemary essential oil | 30 |
| Amyl salicylate | 50 |
| Terpineol Alpha | 10 |
| 2-Ethyl-4,4-dimethyl-1-cyclohexanone | 5 |
| Red thyme essential oil | 15 |
| 10% * Undecalactone gamma | 10 |
| 10% * Verdox ® [8] | 35 |
| (2,2-dimethoxyethyl)benzene | 10 |
| Vertofix ® [9] Coeur | 20 |
| Vetyver essential oil | 30 |
| Ylang Extra | 15 |
| 2,4-Dimethyl-3-cyclohexene-1-carbaldehyde | 10 |
| | 2250 |

* in dipropyleneglycol
[1] 1,2,3,5,6,7-Hexahydro-1,1,2,3,3-pentamethyl-4-indenone; origin: International Flavors & Fragrances, USA
[2] Laevo isomer of dodecahydro-3a,6,6,9a-tetramethyl-naphtho[2,1-b]furan; origin: Firmenich SA, Switzerland
[3] Pentadecenolide; origin: Firmenich SA, Switzerland;
[4] Methyl dihydrojasmonate; origin: Firmenich SA, Switzerland
[5] 1-(octahydro-2,3,8,8-tetramethyl-2-naphtalenyl)-1-ethanone; origin: International Flavors & Fragrances, USA
[6] 2,5-dimethyl-2-indanmethanol; origin: Firmenich SA, Switzerland
[7] 3-Methyl-(4)-cyclopentadecenone; origin: Firmenich SA, Switzerland
[8] 2-Tert-butyl-1-cyclohexyl acetate; origin: International Flavors & Fragrances, USA
[9] Methyl cedryl ketone; origin: International Flavors & Fragrances, USA The addition of 750 parts by weight of perhydro-6,8,8a-trimethyl-1-naphthalenol gives an earthy-Patchouli twist to this masculine woody-herbal fragrance, a little but like real patchouli would do, but that no other synthetic woods are able to give.

The invention claimed is:

1. A compound of formula:

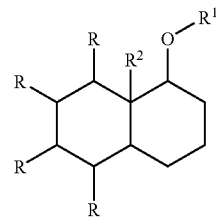

(I)

wherein $R^1$ represents a hydrogen atom or a formyl or acetyl group;

$R^2$ represents a methyl or ethyl group; and each R represents, independently from each other, a hydrogen atom or a methyl group, and at least two of said R are methyl groups.

2. The compound according to claim 1, of formula:

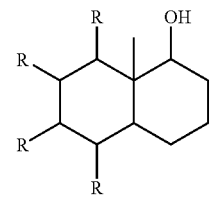

(II)

wherein two R represent hydrogen atoms and the two other R represent methyl groups.

3. The compound according to claim 1, specifically as perhydro-6,8,8a-trimethyl-1-naphthalenol.

4. A perfuming composition comprising:

i) at least one compound of formula

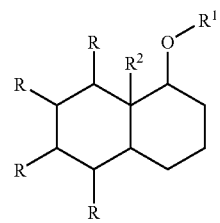

(I)

wherein $R^1$ represents a hydrogen atom or a formyl or acetyl group;

$R^2$ represents a methyl or ethyl group; and each R represents, independently from each other, a hydrogen atom or a methyl group, and at least two of the R substituents are methyl groups;

ii) at least one ingredient selected from the group consisting of a perfumery carrier and a perfumery base; and iii) optionally at least one perfumery adjuvant.

5. The composition according to claim 4, wherein the compound is of formula:

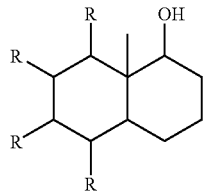

(II)

wherein two R represent hydrogen atoms and the two other R represent methyl groups.

6. The composition according to claim 4, wherein the compound is perhydro-6,8,8a-trimethyl-1-naphthalenol.

7. A perfumed article comprising:
i) at least one compound of formula

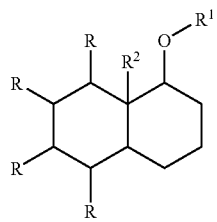

(I)

wherein $R^1$ represents a hydrogen atom or a formyl or acetyl group;
$R^2$ represents a methyl or ethyl group; and
each R represents, independently from each other, a hydrogen atom or a methyl group, and at least two of said R are methyl groups; and
ii) a consumer product base.

8. The perfumed article according to claim 7, wherein the compound is of formula:

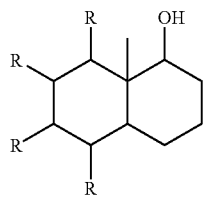

(II)

wherein two R represent hydrogen atoms and the two other R represent methyl groups.

9. The perfumed article according to claim 7, wherein the compound is perhydro-6,8,8a-trimethyl-1-naphthalenol.

10. The perfumed article according to claim 7, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

11. A method to confer, enhance, improve or modify the odor properties of a perfuming composition or of a perfumed article, which method comprises adding to said composition or article an effective amount of at least a compound of formula

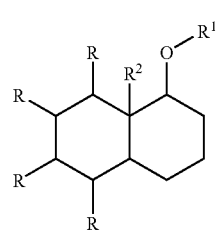

(I)

wherein $R^1$ represents a hydrogen atom or a formyl or acetyl group;
$R^2$ represents a methyl or ethyl group; and
each R represents, independently from each other, a hydrogen atom or a methyl group, and at least two of said R are methyl groups.

12. The method according to claim 11, wherein the compound is of formula:

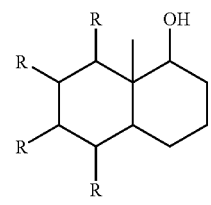

(II)

wherein two R represent hydrogen atoms and the two other R represent methyl groups.

13. The method according to claim 11, wherein the compound is perhydro-6,8,8a-trimethyl-1-naphthalenol.

* * * * *